(12) United States Patent
Shah et al.

(10) Patent No.: US 6,667,409 B2
(45) Date of Patent: Dec. 23, 2003

(54) PROCESS AND APPARATUS FOR INTEGRATING AN ALKENE DERIVATIVE PROCESS WITH AN ETHYLENE PROCESS

(75) Inventors: Minish Mahendra Shah, East Amherst, NY (US); M. Mushtaq Ahmed, Pittsford, NY (US); Raymond Francis Drnevich, Clarence Center, NY (US)

(73) Assignee: Praxair Technology, Inc., Danbury, CT (US)

( * ) Notice: Subject to any disclaimer, the term of this patent is extended or adjusted under 35 U.S.C. 154(b) by 186 days.

(21) Appl. No.: 09/963,446

(22) Filed: Sep. 27, 2001

(65) Prior Publication Data

US 2003/0060642 A1 Mar. 27, 2003

(51) Int. Cl.$^7$ .................... C07D 301/08; C07D 301/10
(52) U.S. Cl. ................ 549/532; 549/534; 549/541
(58) Field of Search ................ 549/532, 534, 549/541

(56) References Cited

U.S. PATENT DOCUMENTS

| | | | |
|---|---|---|---|
| 4,769,047 A | 9/1988 | Dye | |
| 4,879,396 A | 11/1989 | Ozero | |
| 4,904,807 A | 2/1990 | Ozero | |
| 5,233,060 A | 8/1993 | Pendergast et al. | |
| 5,318,759 A | 6/1994 | Campbell et al. | |
| 5,518,527 A | 5/1996 | Tomizuka et al. | |
| 5,519,152 A | 5/1996 | Gorcester | |
| 5,817,841 A | 10/1998 | Baker et al. | |
| 5,952,523 A | 9/1999 | Papavassiliou et al. | |
| 6,040,467 A | 3/2000 | Papavassiliou et al. | |

*Primary Examiner*—Ba K. Trinh
(74) *Attorney, Agent, or Firm*—Iurie Schwartz

(57) ABSTRACT

An integrated process and apparatus for integrating an alkene derivative process, such as ethylene oxide process, with an ethylene process so that any ethylene entrapped in the purge stream of the alkene derivative process can be effectively recovered through the ethylene process portion of the integrated process.

17 Claims, 4 Drawing Sheets

PROCESS AND APPARATUS FOR INTEGRATING AN ALKENE DERIVATIVE PROCESS WITH AN ETHYLENE PROCESS

FIELD OF THE INVENTION

This invention relates to a process and apparatus for integrating an alkene derivative process, such as an ethylene derivative process, with an ethylene process.

BACKGROUND OF THE INVENTION

Many well-known processes are used for the manufacturing of alkene derivatives such as ethylene oxide and vinyl acetate monomers. Generally, these processes employ a purge to prevent build up of inerts in the alkene derivative production system. This purge stream can contain ethylene concentrations as high as 30 mole percent in an ethylene oxide process and as high as 80 mole percent in a vinyl acetate process. Depending on the process used, the amount of ethylene lost in the purge could be 1% or more of the amount required for the derivative process. The prior art has generally focused on recovering ethylene from the purge stream using separation schemes employing absorption, adsorption or membrane systems and could be located near the alkene derivative reactor of the alkene derivative process. For example, ethylene, oxygen and other reactants may react to produce an alkene derivative from a reactor. Process gas containing unconverted reactants in process gas treatment unit may be treated to remove carbon dioxide and then recycled back to the reactor. A purge gas stream from the process gas treatment may be vented to prevent build-up of inert or undesirable components in the process loop. While some plants incinerate the purge stream, others recover valuable ethylene from the purge stream for recycle to the reactor. An ethylene recovery unit may be used for this purpose, producing ethylene rich stream for recycle to the reactor and ethylene depleted stream, which is vented to reject the inerts. In some cases, ethylene depleted stream may be incinerated or used as a fuel. The ethylene recovery unit may be an absorption means, membrane means, pressure swing adsorption (PSA) means alone or in combination with a cryogenic unit.

U.S. Pat. No. 4,769,045 discloses a process for the direct oxidation of ethylene to ethylene oxide, in which ethylene is recovered from normally vented gas by contacting first with an activated carbon adsorbents and then by pressure swing adsorption with a zeolitic molecular sieve adsorbent.

U.S. Pat. No. 5,519,152 discloses a process of manufacturing ethylene oxide. Ethylene and free oxygen are reacted in the presence of methane, carbon dioxide, and argon in a reactor to form an effluent comprising ethylene oxide. The effluent is then withdrawn and ethylene oxide is removed from the effluent to obtain a recycle stream. The carbon dioxide and argon are removed from the recycle stream to obtain a treated recycle stream, which is supplied to the reactor along with additional reactants and methane.

U.S. Pat. No. 5,518,527 discloses a method for recovering ethylene from ethylene-containing vent gas from a plant for production of ethylene oxide, wherein ethylene is separated from saturated hydrocarbons such as methane, ethane and oxygen and then recovered efficiently. In this method, the vent gas contacts with molecular sieve carbon to selectively adsorb ethylene without substantial adsorption of the oxygen contained in the vent gas. The ethylene is then desorbed and recovered.

U.S. Pat. No. 4,904,807 discloses a process for producing ethylene oxide, which minimizes unreacted ethylene losses through the use of semi-permeable membrane units, thereby allowing an effective, selective removal of argon from the process cycle gas, without significant ethylene losses.

U.S. Pat. No. 4,879,396 discloses a process for producing ethylene oxide utilizing suitable semipermeable membrane units to selectively remove desired amounts of both carbon dioxide and argon diluents from the reaction recycle gas. This process makes available a much cheaper low purity oxygen source notwithstanding feed purge loss.

U.S. Pat. No. 5,817,841 discloses a process and apparatus for ethylene oxide production. A membrane unit containing a membrane selectively permeable to ethylene over argon is used to recover ethylene from the argon purge stream.

U.S. Pat. No. 5,233,060 discloses a direct-oxidation ethylene oxide process by reacting a feed gas stream including ethylene and a commercially-pure oxygen in one or more reactors and absorbing out ethylene oxide from the product stream from the one or more reactors in a first absorption zone. Unreacted ethylene is then removed from an ethylene-rich argon purge gas stream via an adsorber and a stripper in combination. Recovered ethylene is recycled to the feed gas stream. An ethylene-lean argon purge gas stream is removed.

U.S. Pat. No. 5,952,523 discloses a method for producing vinyl acetate using ethylene, acetic acid and argon containing oxygen that maximizes selectivity and minimizes ethylene loses to purge.

The prior art generally involves dedicated separation units for ethylene recovery. In many cases, ethylene is obtained at low pressure and a dedicated compressor must be used to recompress it to the operating pressure of the reactor. Due to incomplete recovery, a small volume of vent stream containing hydrocarbon is still generated. This vent gas must be either incinerated or burned as a fuel. Also, if the recovered ethylene contains impurities, complex controls will be required to prevent their build up in the recycle loop.

It is an object of the present invention to provide a process and apparatus for recycling ethylene from the purge stream of an alkene derivative process.

It is another object of the present invention to provide a process and apparatus for integrating an alkene derivative process with an ethylene process to effectively minimize alkene loss in the purge stream of the alkene derivative process.

It is yet another object of the present invention to provide a process and apparatus for recovering ethylene from the purge stream of an ethylene oxide process.

It is yet another object of the present invention to provide a process and apparatus for recovering the ethylene from the purge stream of a vinyl acetate monomer process.

SUMMARY OF THE INVENTION

This invention is related to a process for integrating an alkene derivative process with an ethylene process comprising the steps of (a) feeding a hydrocarbon feedstock to an alkene process to produce alkene; (b) reacting alkene with oxygen and reactants to produce an alkene derivative such as an ethylene derivative, a propylene derivative and other derivatives; (c) purifying the alkene derivative to produce a purified alkene derivative segment and an unconverted reactant-based segment; (d) recovering and removing the purified alkene derivative; (e) removing undesirable by-product gas from the unconverted reactant segment and feeding a first portion of the treated unconverted reactant segment to the reacting process in step (b) and then removing from the second portion of the treated unconverted reactant segment any components that are incompatible for use as feedstock in step (a); and (f) feeding the further treated second portion of the unconverted reactor segment of step (e) with the feedstock of step (a) into the alkene process.

This invention also relates to an apparatus for integrating an alkene derivative process with an alkene process comprising an alkene process having means for producing alkene from hydrocarbon feedstock and means for discharging the alkene to a reactor unit. The reactor unit has means for producing an alkene derivative from oxygen, alkene from an alkene source and reactants, and means for discharging the alkene derivative to a product recovery unit. The process gas treatment unit having means for removing undesirable gas from the unconverted reactants and means for discharging a portion of the undesirable gas-free unconverted reactants to the reactor section and the remainder to a purge gas treatment unit. The purge gas treatment unit has means for removing components that are incompatible for use in the alkene process and means for discharging the component-free unconverted reactants to the alkene process.

The current invention combines the alkene derivative process with the alkene process. The alkene derivative process purge stream is sent to the alkene process train. The alkene process train cracks hydrocarbons to produce alkenes (such as ethylene and propylene) for the alkene derivative processes. As will be discussed, the purge stream enters the train at one of several possible stages and travels with the hydrocarbon feed. Inerts from the purge stream are removed at a demethanization stage of the alkene process. The alkenes are then sent to the alkene derivative processes, while the separated inerts can then be sent off as usable fuel streams.

BRIEF DESCRIPTION OF THE DRAWINGS

Other objects, features and advantages will occur to those skilled in the art from the following description of preferred embodiments and the accompanying drawings, in which.

DETAILED DESCRIPTION OF THE PREFERRED EMBODIMENT

Figure 1:
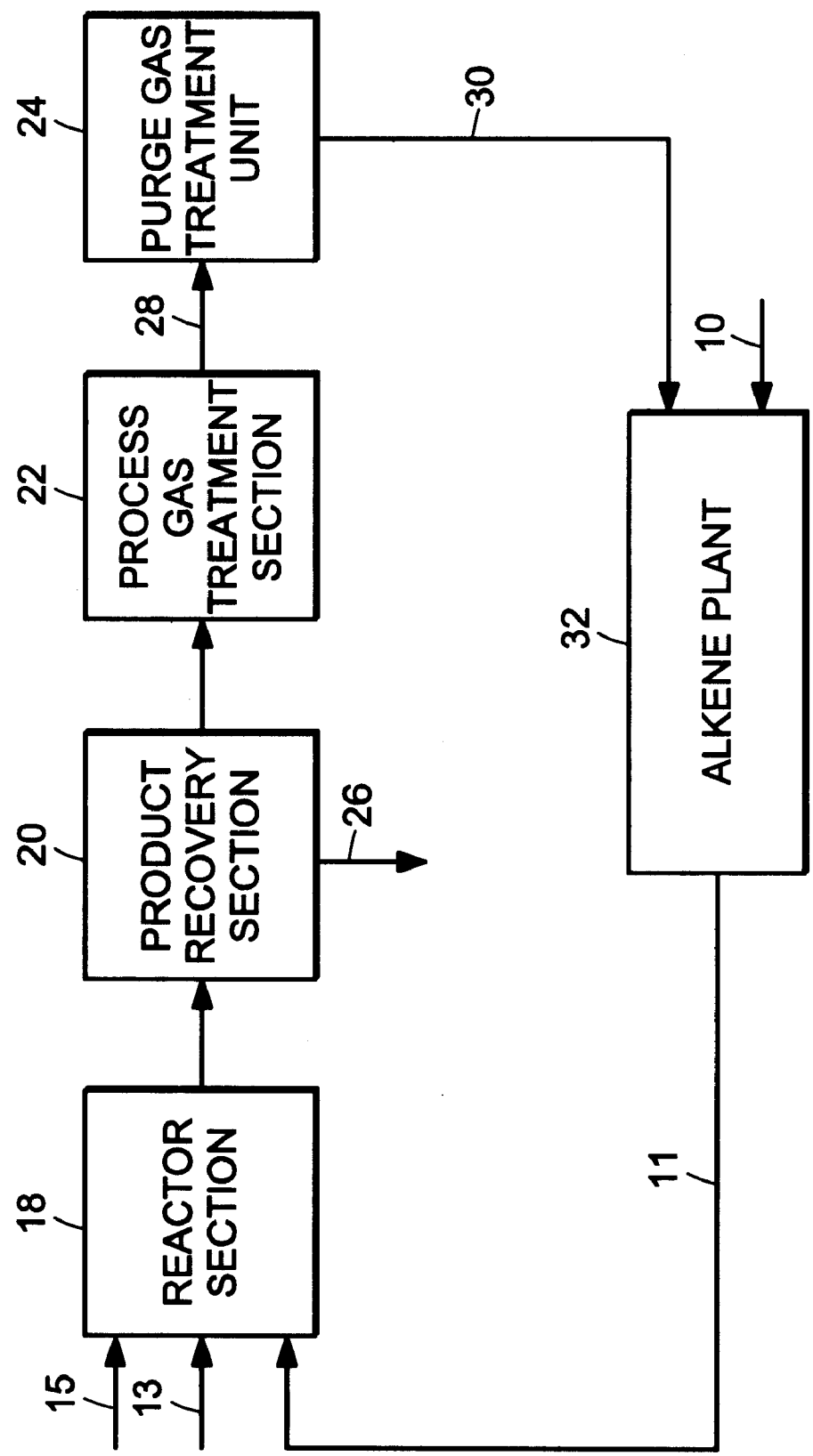
FIG. 1 is a schematic representation of an alkene derivative process integrated with an alkene process in accordance with the invention.

As shown in FIG. 1, alkene is recovered from an alkene derivative process purge through integration of the alkene and alkene-derivative processes. For this purpose, the alkene derivative process purge is first treated to remove any undesirable component prior to processing it in the alkene source (i.e., an alkene plant) for alkene recovery. Due to small volume of purge stream (generally less than 1%) relative to the volume of gas being separated in the alkene source, there generally will not be any need to resize the separation train of alkene process. Thus, the process of the subject invention is cost-effective. In addition, by integrating alkene and alkene derivative processes, more complete recovery of alkene (generally more than 90%) is achieved, and the volume of hydrocarbon containing vent, if any, from the alkene derivative process is significantly reduced.

Hydrocarbon feedstock 10 is processed in the alkene plant 32 to produce alkenes such as ethylene and propylene. Examples of alkene source feed include ethane, propane, butane, and naphtha. The same reference numbers have been used to identify the same parts in the drawings of this application. Alkene product stream 11 is sent to the alkene derivative reactor 18 as feed. This alkene reacts with oxygen 13 and other reactant(s) 15 to make the alkene derivative product. For example, ethylene oxide is manufactured by reacting ethylene with oxygen, and vinyl acetate is manufactured by reacting ethylene with oxygen and acetic acid. Alkene derivative product in the reactor effluent is purified and recovered as stream 26 from the product recovery section 20. The process gas containing unconverted reactants is treated in the process gas treatment section 22 to remove the reaction byproducts, such as carbon dioxide, and recycled back to the reactor, and purge stream 28 from the process gas treatment section is established to prevent build up of inerts in the process loop. This purge gas 28 is processed in purge gas treatment unit 24 to remove any components that are incompatible with alkene plant 32. One example of such components is oxygen, which can be removed by chemical reactions that consume oxygen, and/or oxygen selective adsorbents yielding oxygen-free gas. The stream 30 is passed from unit 24 to alkene plant 32.

The reaction system can be designed to carry out catalytic chemical reactions between hydrocarbons and oxygen, and/or between externally added hydrogen and oxygen to consume all of the oxygen. If only alkene reacts with all of the oxygen to form complete combustion products, then that will translate into an alkene loss of generally less than 10% of alkene contained in the purge stream. The remaining alkene is then recovered in the alkene plant separation system 32.

Figure 3:
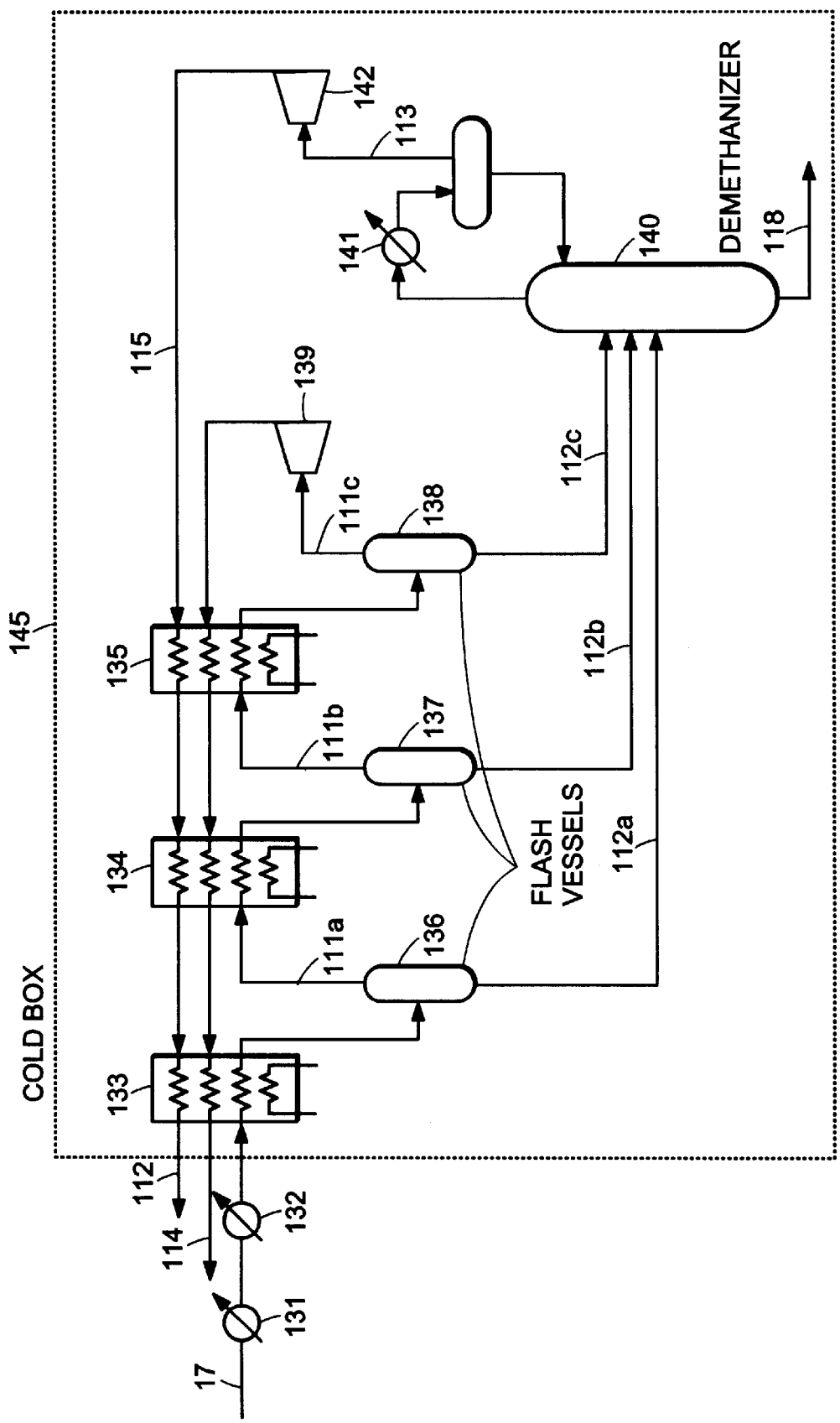
FIG. 3 is a schematic of a representation of a demethanization section of the ethylene process of FIG. 1.

The reaction system can also be designed and operated such that hydrogen reacts preferentially with oxygen, thus minimizing alkene losses to oxidation products. The reactor effluent generally contains alkene, argon, methane, nitrogen, hydrogen, carbon dioxide and possibly some carbon monoxide. The stream is sent to the alkene separation train where ethylene and propylene are separated from ethane and higher hydrocarbons and other alkenes, carbon dioxide, carbon monoxide, methane and hydrogen. An additional component that is not present in the conventional alkene separation system is argon. After carbon dioxide and water removal, crude alkene stream can be separated in a cryogenic section. The cryogenic section separates hydrogen first and the fuel stream (mostly methane) from the alkene stream. Since argon and nitrogen are more volatile than methane, they are expected to separate with methane in an overhead of a demethanizer column as shown in FIG. 3 and discussed below. In this way, the subject invention uses alkene plant's existing separation capability to reject argon and nitrogen from the purge stream while recovering most of the alkene (generally more than 90%).

Figure 2:
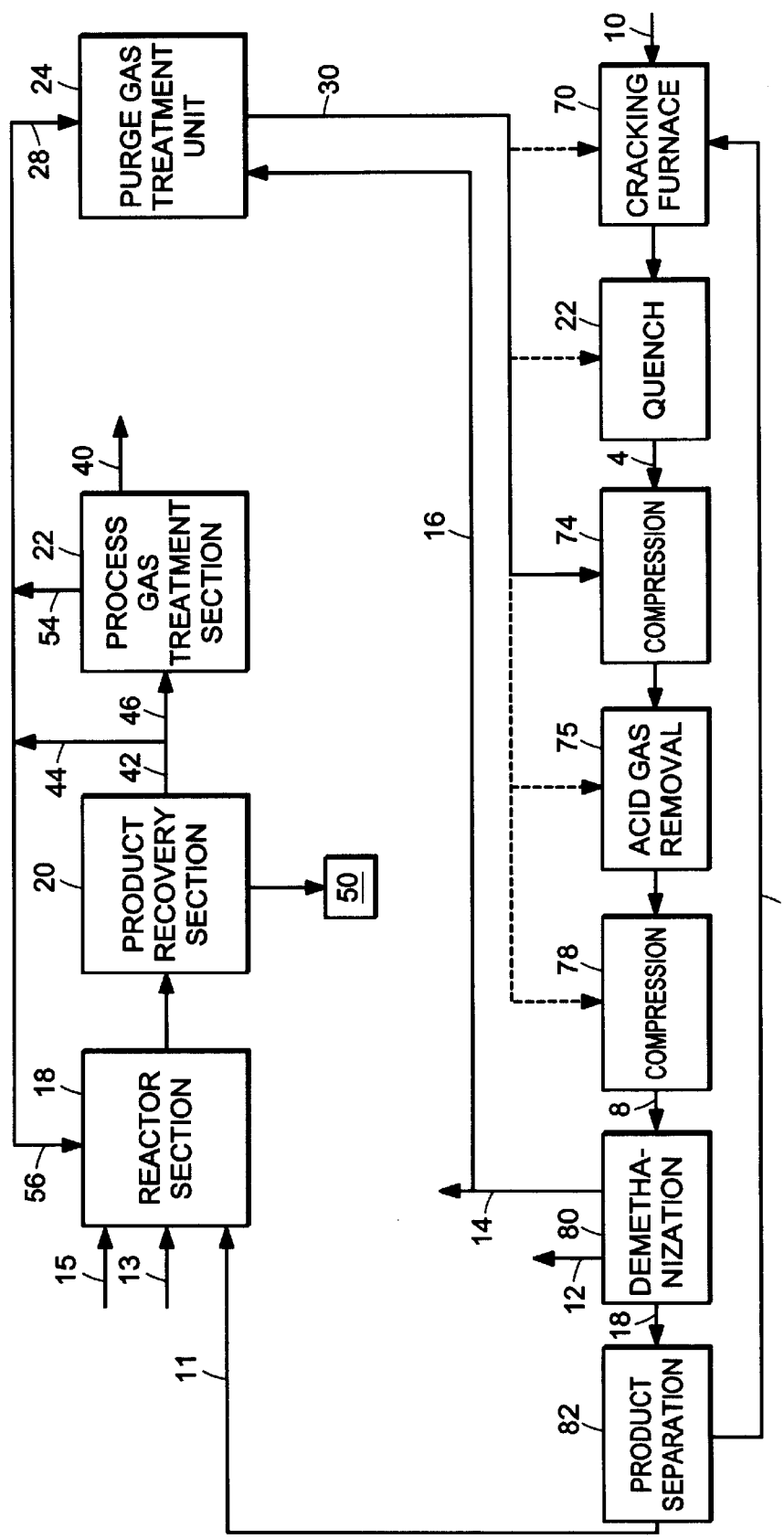
FIG. 2 is a schematic representation of a process for ethylene recovery from an ethylene oxide process by integrating the ethylene oxide process with the ethylene process.

FIG. 2 is a schematic illustrating the integration of ethylene oxide (alkene derivative) and ethylene processes to recover ethylene from the ethylene oxide process purge. A novel feature of this invention is the integration of the alkene derivative process and the ethylene process. Additionally, a novel deoxo treatment is used in the alkene derivative process. After carbon dioxide 40 is removed from the reactor effluent, a portion of the stream becomes a purge stream. The deoxo unit removes oxygen from the purge, which is then sent to the ethylene process for ethylene recovery. A brief summary of the ethylene manufacturing process comprises: (a) cracking hydrocarbon feedstock 10 in section 70 to produced cracked gas; (b) cooling in section 22, compression in section 74 and clean up (acid gas removal) in 75 and further compression in section 78; (c) separating hydrogen, fuel components (such as methane and carbon monoxide), inert components (such as argon and nitrogen) in the demethanizer unit 80; and (d) separating ethane, ethylene and other products in the product separation section 82.

A brief summary of the ethylene oxide manufacturing process comprises: (e) production and recovery of ethylene oxide from ethylene and oxygen in the reaction section 18 and product recovery section 20; (f) removing carbon dioxide from reactor effluent gas in section 22, and recycle of treated gas; (g) processing of the purge gas to remove oxygen in the purge treatment unit 24; and (h) feeding treated purge gas to the compression and clean-up section of the ethylene process for recovery of ethylene in the subsequent separation sections.

In the ethylene process, hydrocarbon feedstock 10 and ethylene process recycle stream 84 from product separation system 82 are thermally cracked in the presence of steam in cracking furnace 70. Reaction products include ethylene, methane, hydrogen, other alkenes and alkanes, carbon monoxide, carbon dioxide, water, sulfur and nitrogen containing species (if sulfur and nitrogen are present in the feed).

Heat for endothermic cracking reactions is generally supplied by using methane-rich fuel stream from the separation system as fuel in cracking furnaces. Cracking products are quickly cooled and sent to fractionating towers to recover gasoline and light oil fractions. Cracked gas 4 from the quenching and light oil recovery section 22 is sent to the compression and clean-up sections 74, 75 and 78. The cracked gas is compressed and cleaned to remove water and acid gases. A multi-stage compressor can be used to compress the gas stream 4 to a final pressure range of about 450–500 psia. The acid gas removal system 75 is located between the third and fourth stages (74 and 78) of the compressor. A treated stream 30 (described later) is also introduced into section 74 for ethylene recovery. The stream 30 is added at appropriate locations in the compressor train, depending on its pressure, but prior to acid gas removal system which includes absorber-stripper for acid gas removal (for example, using 15% monoethanolamine solution) followed by a caustic scrubber to remove any remaining carbon dioxide. The carbon dioxide-free gas is compressed further in the fourth stage of the compressor and then dried to remove moisture. Dried and cleaned gas 8 is processed in the demethanization section 80 to produce product separation section feed 18. A fuel gas stream 12, rich in methane, is sent to the plant fuel heater. The crude hydrogen stream from the demethanization section is divided into two portions, stream 14 (sent to recover high purity hydrogen or to a fuel header) and stream 16 sent to the purge treatment unit 24. The oxygen in stream 28 is consumed in the purge treatment unit by reactions with hydrogen in stream 16 and hydrocarbons present in both stream 28 and stream 16. The resulting oxygen depleted stream 30 is routed to the ethylene process for recovering ethylene and rejecting inerts originally present in stream 28. Ethylene 11 from the product separation section 82 is supplied to the ethylene oxide reactor 18 in the alkene derivative process.

In the ethylene oxide process, ethylene 11, oxygen 13, ballast gas 15 and recycle stream 56 are fed to a fixed bed reactor. The heat of reaction is removed, for example, by boiling kerosene on the outside of the catalyst packed tubes in the reactor 18. The extent of conversion is generally kept low. Reactions between oxygen and ethylene results in the formation of ethylene oxide, as well as carbon dioxide and water. The reactor effluent is sent to an absorber for ethylene oxide recovery. The product-free effluent 42 is split into two portions. One portion 46 is sent to carbon dioxide recovery section 22 and other portion 44 bypasses that section. Carbon dioxide is removed from the gas stream 46 by absorption in hot potassium carbonate solution. Waste carbon dioxide is vented as stream 52. A small portion 28 of overhead stream 54 from absorber is purged to prevent build up of argon in the loop. The remainder is combined with stream 44 and recycled back to reactor 18 as stream 56.

According to the present invention, the purge stream 28 is sent to the purge processing section (deoxo) 24 for removal of oxygen, and then routed to ethylene process. The purge treatment unit 24 contains one or more catalytic reactors to consume oxygen, preferably one reactor. Preferably, the catalytic reactor is a catalytic deoxo reactor to emphasize the removal of oxygen from the reactor feed stream. The catalyst can be a silver catalyst used in the ethylene oxide reactor or another commercial chemical oxidation catalyst. The reactor can be designed to contain a single catalyst or more than one catalyst. The reactor can operate at a pressure in the 50 to 1000 psia range, preferably at a pressure that does not require compression of the purge stream. The catalyst bed temperature can be maintained in the 500° F. to 2000° F. range, preferably 800° F. to 1600° F., more preferably between 1200° F. to 1400° F. to consume all of the oxygen by forming combustion products.

Several alternative embodiments are available by the use of this FIG. 2. Effluent gas 30 may be fed to a number of other processes in the present section as shown by the dashed lines. In one such embodiment, effluent gas 30 is fed to quench section 22. In another embodiment, effluent gas 30 is fed to cracking section 70 either alone or mixed with ethylene recycle 84. In yet another embodiment, depending upon the effluent gas pressure, effluent gas 30 may be added directly to acid gas removal section 75 or to higher pressure compression section 78.

FIG. 3 presents one example of the FIG. 2 demethanizer section 80 to separate crude hydrogen stream and methane rich fuel stream from the cracked gas. Dried and cleaned gas 17 is cooled first by water in cooler 131 and then by propylene refrigerant in chiller 132 and the gas sent to the cryogenic cold box 145, in which it is progressively cooled with returned product streams (fuel stream and crude hydrogen stream) and propylene and ethylene refrigerants. The chilling train consist of heat exchangers 133, 134 and 135 and separators 136, 137 and 138 to cool the gas. Liquids 112a, 112b and 112c from the separators are fed to the demethanizer tower 140 while vapors 111a and 111b are further cooled in the next cooler in the series. Overhead gas 111c from the final flash vessel 138, is mainly crude hydrogen with small quantities of inert components (nitrogen and argon) introduced from stream 30 (FIG. 2). The crude hydrogen stream 111c is expanded in expander 139 and then warmed in the heat exchangers 133, 134 and 135. The warmed hydrogen stream 114, also referred to as crude hydrogen, is sent to PSA to recover high purity hydrogen. In the demethanizer tower 140, methane and inert components (argon and nitrogen) in the liquid feeds are stripped off. The overhead from the demethanizer contains mainly methane and hydrogen. Some argon and nitrogen from the ethylene derivative process purge stream end up in the methane-rich fuel stream. The overhead fuel-rich stream 113 is expanded in the expander 142, then stream 115 is warmed through heat exchangers 135, 134 and 133 and removed as fuel stream 112. The $C_{2+}$ product stream 118 from the bottom of the demethanizer is sent to the product separation section 82 where ethylene 112, ethane rich recycle stream 38 and other products are separated (see, FIG. 2).

Figure 4:
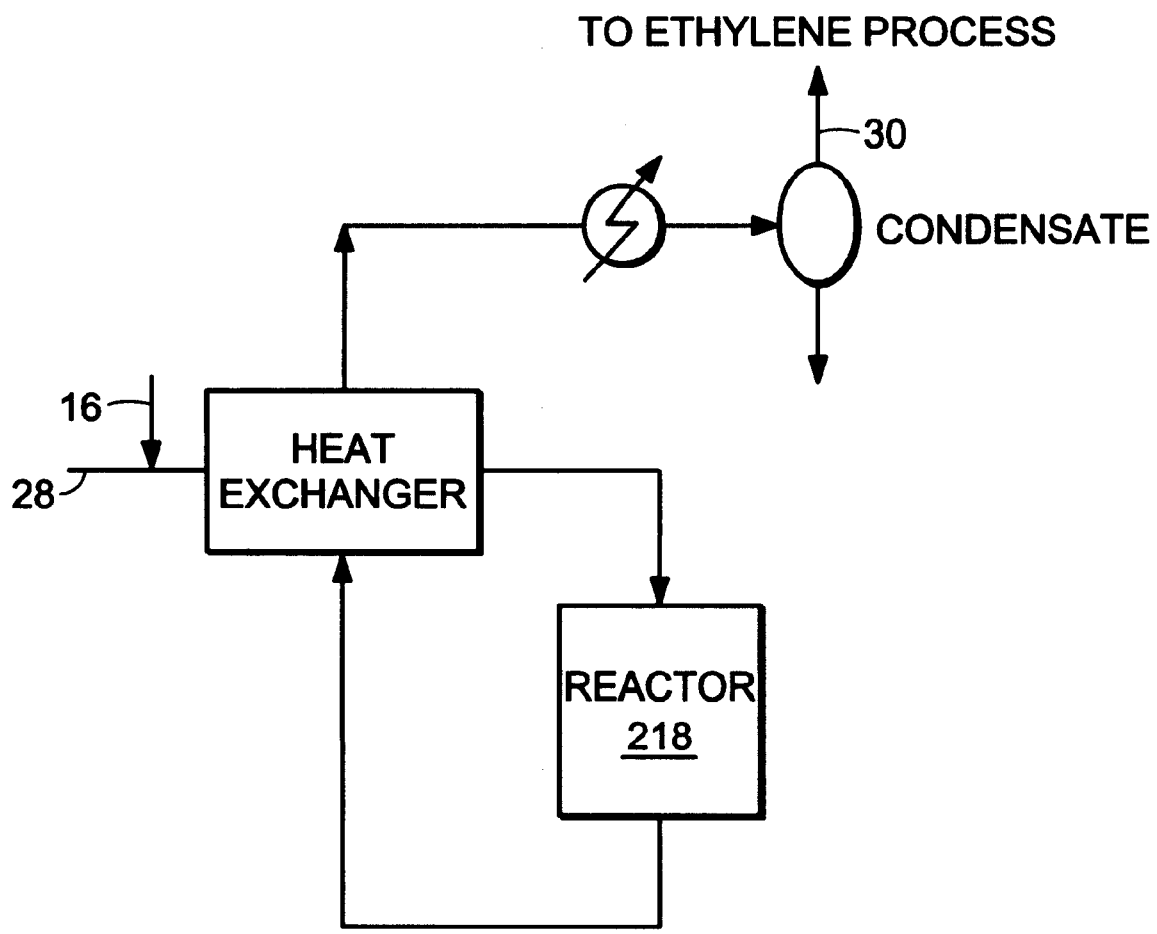
FIG. 4 is a schematic representation of an ethylene oxide process coupled to the quench section of an ethylene process.

FIG. 4 is a simplified schematic of the purge processing unit 24. The purge 28 from the ethylene oxide process and crude hydrogen 16 from the ethylene process are heated and fed to a fixed bed reactor, 218, or preferably, a catalytic deoxo reactor. The reactor effluent is first cooled by exchanging heat with the feed, and then further cooled to remove water and water soluble species before feeding it to the ethylene process compression and clean-up section. This way a majority of the oxygen is consumed by reaction with hydrogen, thus minimizing ethylene loss. The effluent gas 30 from purge treatment unit 24 containing ethylene, argon, methane, carbon dioxide, water, hydrogen and carbon monoxide is sent to the compression section 74 in the ethylene process.

Another embodiment shows integration schemes are also applicable to vinyl acetate manufacturing processes. FIG. 2 is used to describe this embodiment. In this case, ethylene 11, oxygen 13, and acetic acid 15 is reacted to produce vinyl acetate monomer 50. The effluent gas 42 is split into two fractions 44 and 46. Carbon dioxide gas 40 is removed from stream 46 and the treated gas 54 is recycled along with stream 44. A purge 28, a minor portion of stream 54, is established to prevent build up of inerts in the process loop. This purge 28 is treated in the purge treatment unit 24 to remove oxygen, thus producing oxygen-free stream 30 from which ethylene is recovered in the ethylene process. Compared to an ethylene oxide process, the vinyl acetate monomer process operates at lower pressure, typically in the 50 to 150 psia range and produces a lower pressure purge. Thus in this case, the effluent gas 30 from the purge treatment unit 24 is sent to the quench section 22. Other options include feeding it to the cracking section 70, or compressing it in the urge treatment section 24.

In the integration of the ethylene oxide and ethylene processes, and the vinyl acetate monomer and ethylene processes, several options exist to remove oxygen. FIG. 4 showed one embodiment employing chemical reactions. The heat released due to exothermic reactions in the catalyst bed results in temperature rise of the flowing gas. One embodiment to control the catalyst bed temperature is to regulate the reactor feed temperature by splitting the feed stream 28 into two streams, one of which bypasses the heat exchanger recovering heat from the reactor effluent. Other embodiments are possible, such as cooling the reactor effluent before feeding it to the heat exchanger, thereby recovering heat from a portion of the reactor effluent. Although only a few embodiments are discussed, several other possibilities, including heat exchange means in the reactor, will be obvious to those skilled in the art.

The purge treatment unit reactor design 24 employing more than one catalyst bed may be desirable. For example, the purge stream 28 can be treated first with a less expensive catalyst to consume the bulk of the oxygen, then a more expensive catalyst is used to assure that all the oxygen has been consumed before passing it on to the ethylene process for ethylene recovery. Either fixed bed or fluidized bed reactors can be employed. FIG. 4 shows the use of crude hydrogen 15 from the ethylene process for reaction with oxygen to produce oxygen-free effluent gas 30. The use of a hydrogen-based gas, such as crude hydrogen or higher purity hydrogen, is not a requirement for recovering ethylene from the ethylene-derivative process purge. For example, other reactants or adsorbent materials can be used to remove oxygen from purge 28. Another way is to use a combination of chemical reaction and adsorption processes to remove oxygen from the ethylene derivative process purge before sending it to the ethylene process.

In the prior art of a non-integrated ethylene oxide process, high-purity oxygen is generally preferred to minimize purge stream volume and hence, ethylene losses. By providing means to fully recover ethylene in the integrated process of the subject invention, it is possible to lessen the oxygen purity requirements in the ethylene derivative process. Introduction of additional amounts of inert components (such as argon and nitrogen) from low-purity oxygen in the process loop requires higher purge flow which results in higher ethylene losses in non-integrated processes. In the subject invention, this will not be a problem since 90% or higher of ethylene in the purge could be recovered in the ethylene process.

Although the embodiment was discussed with the examples of ethylene derivatives, it is also applicable for many alkene derivative processes. For example, this invention is applicable to propylene derivatives such as propylene oxide.

Those skilled in the art will recognize that numerous changes may be made to the process described in detail herein, without departing in scope or spirit from the present invention as more particularly defined in the claims below.

What is claimed is:

1. A process for integrating an alkene derivative process with an alkene process comprising the steps:
   (a) thermally cracking a hydrocarbon feedstock to produce alkene;
   (b) reacting said alkene with oxygen and reactants to produce an alkene derivative;
   (c) purifying said alkene derivative to produce a purified-alkene derivative segment and an unconverted segment;
   (d) recovering and removing said purified-alkene derivative;
   (e) removing waste gas from said unconverted segment to form a first portion of treated reactant segment and a second portion of unconverted reactant segment; and
   (f) feeding said second portion of unconverted reactor segment of step (e) along with the feedstock of step (a) into an alkene process.

2. The process of claim 1 wherein the alkene derivative is ethylene derivative.

3. The process of claim 1 wherein the alkene derivative is propylene derivative.

4. The process of claim 2 wherein the ethylene derivative is ethylene oxide.

5. The process of claim 3 wherein the propylene derivative is propylene oxide.

6. The process of claim 1 wherein alkene the alkene is ethylene, the reactant in step (b) is acetic acid and the alkene derivative is vinyl acetate monomer.

7. The process of claim 1 wherein the waste gas in step (e) is carbon dioxide.

8. The process of claim 1 wherein the alkene derivative in step (b) contains alkene and at least one material selected from the group argon, methane, nitrogen, hydrogen, carbon dioxide and carbon monoxide.

9. The process of claim 1 wherein the hydrocarbon feedstock of step (a) comprises at least one material selected from the group consisting of ethane, propane, butane and naphtha.

10. The process of claim 1 wherein the second portion of the unconverted reactant segment contains oxygen and the process further includes the step of removing said oxygen from the unconverted second reactant segment to form an oxygen-free second portion before feeding the oxygen-free second portion to the alkene process.

11. The process of claim 1 wherein said alkene process comprises an in line coupling of cracking unit, quenching unit, first compressing unit, acid gas unit, second compressing unit, demethanization unit and product separation unit, and wherein the second portion of unconverted reactant segment is fed into the first compressing unit of the alkene process and is treated along with the feedstock through said alkene process to produce the alkene.

12. The process of claim 11 wherein a stream from the demethanization unit contains hydrogen and at least one material selected from the group consisting of methane, carbon monoxide, argon and nitrogen, and wherein a portion of said stream is fed back into the second portion of the unconverted reactant segment and said components that are incompatible for use as feedstock in step (a) are removed.

13. The process of claim 12 wherein the product separation unit contains alkene and at least one material selected from the group consisting of ethane, propane and butane and wherein said alkene is separated and used in step (b) to produce an alkene derivative.

14. The process of claim 10 wherein step (e) comprises removing oxygen by chemical reaction with a hydrogen-based gas.

15. The process of claim 10 wherein step (e) comprises adsorption by an adsorbent and oxygen removal.

16. The process of claim 1 wherein the thermal cracking in step (a) comprises an in line coupling of cracking unit, quenching unit, first compressing unit, acid gas unit, second compressing unit, demethanization unit and product separation unit.

17. The process of claim 1 wherein the the removal of waste gas in step (e) comprises feeding the second portion of unconverted reactant segment into a first compressing unit of the alkene process to treat the second portion along with the feedstock in said alkene process to produce the alkene.

* * * * *

UNITED STATES PATENT AND TRADEMARK OFFICE
CERTIFICATE OF CORRECTION

PATENT NO. : 6,667,409 B2
DATED : December 23, 2003
INVENTOR(S) : Shah et al.

It is certified that error appears in the above-identified patent and that said Letters Patent is hereby corrected as shown below:

Column 8,
Line 53, please delete the first occurrence of the word "alkene".

Signed and Sealed this

Sixth Day of April, 2004

JON W. DUDAS
*Acting Director of the United States Patent and Trademark Office*